(12) United States Patent
Kitamura et al.

(10) Patent No.: US 11,950,785 B2
(45) Date of Patent: Apr. 9, 2024

(54) ISCHEMIA CONTROL DEVICE

(71) Applicant: OLYMPUS MEDICAL SYSTEMS CORP., Tokyo (JP)

(72) Inventors: Ojiro Kitamura, Hachioji (JP); Masato Narisawa, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 48 days.

(21) Appl. No.: 17/546,452

(22) Filed: Dec. 9, 2021

(65) Prior Publication Data
US 2022/0257254 A1  Aug. 18, 2022

Related U.S. Application Data

(60) Provisional application No. 63/149,684, filed on Feb. 16, 2021.

(51) Int. Cl.
*A61B 17/122* (2006.01)
(52) U.S. Cl.
CPC ................................. *A61B 17/122* (2013.01)
(58) Field of Classification Search
CPC ............ A61B 17/122; A61B 17/12013; A61B 2017/00017; A61B 2017/00115; A61B 2017/00398
See application file for complete search history.

(56) References Cited

U.S. PATENT DOCUMENTS

| 2012/0211542 | A1* | 8/2012 | Racenet | A61B 17/07207 |
| | | | | 227/175.1 |
| 2014/0107697 | A1* | 4/2014 | Patani | A61B 17/282 |
| | | | | 606/208 |
| 2016/0206318 | A1 | 7/2016 | Kung-Chen | |

FOREIGN PATENT DOCUMENTS

JP        2016-165427 A        9/2016

\* cited by examiner

*Primary Examiner* — Shaun L David
*Assistant Examiner* — Rachael L Geiger
(74) *Attorney, Agent, or Firm* — Morgan, Lewis & Bockius LLP

(57) ABSTRACT

An ischemia control device is connected to a control unit that receives inputs from sensors and other surgical devices that senses patient conditions. The control unit uses the data inputs, as well as direct inputs from the medical operators, to output opening and closing instructions to the ischemia control device. The actuator on the ischemia control device receives the opening and closing instructions and manipulates the ischemia control device. The ischemia control device can be automatically operated using the sensed information to intermittently and alternately achieve ischemia of the organs and reperfuse the organs and, thereby, protect the organs from being damaged by the ischemia.

20 Claims, 7 Drawing Sheets

ISCHEMIA CONTROL DEVICE

RELATED APPLICATION DATA

This application is based on and claims priority under 35 U.S.C. § 119 to U.S. Provisional Application No. 63/149,684, filed on Feb. 16, 2021, the entire contents of which is incorporated herein by reference.

FIELD OF DISCLOSURE

The present disclosure relates to a devise used for controlling ischemia of certain organs during a medical surgery. The ischemia device is equipped with sensors and other features to sense parameters associated with the state of the organs for which ischemia control is to be applied during the medical surgery. The ischemia control device uses the sensed parameters to automatically operate and control ischemia of the organs or recirculate blood stream to protect the organs from being damaged by the ischemia.

BACKGROUND

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

FIG. 7 is a figure of a device for restricting the blood flow of an area in a subject in the related art (U.S. Pat. App. Pub. No. 2016/0206318A1). The related art device is comprised of a bolt 110, restrictor 120, and a strip 130 and used in surgical procedures, such the Pringle maneuver in hepatoectomy. During the operation, one end of the strip 130 is coupled to the restrictor 120 to form a loop surrounding the blood vessels (i.e. portal triad) aimed to achieve ischemia. By driving the bolt 110 into the restrictor 120, the loop of the strip 130 would be tightened, thereby restricting the blood flow of the portal triad supplying blood stream to the liver. This restriction of blood flow achieves ischemia of the liver. Further, to prevent the liver from being severely damaged due to long term ischemia during the surgery, the liver needs to be reperfused with blood from time to time. The bolt 110 may be loosened to release the loop of the strip 130 to achieve blood reperfusion of the portal triad. By re-adjusting the tightness of the bolt 130, the blood flow going into the liver may be intermittently restricted in accordance with the needs during the medical surgery.

FIG. 8 is a figure of another device for restricting the blood flow of an area in a subject in the related art (Japanese Pat. Pub. No. 2016-165427A). The related art vascular clamp 3 includes a first rod body 1 and second rod body 2, a belt-like body 4, a connecting part 5, and a ring-like grip force adjusting member 6. The proximal ends of the first rod body 1 and second rod body 2 (la, 2a) are connected by the connecting part 5, which also serves as a fulcrum for restricting the blood flow. A belt-like body 4 extends from a distal end of the second body 2 (2b) to the outer ridge 2d of the second rod body 2 and connects at its tip 4a. The distal ends of the first rod body 1 and second rod body 2 (1b, 2b) are connected by the a ring-like grip force adjusting member 6 that passes between the belt-like body 4 and the second rod body 2 and tightens the distal ends of the first rod body 1 and second rod body 2 (lb, 2b) towards each other. The abutting surfaces 1c and 2c squeezes the hepatoduodenal ligament 8 to achieve the goal of the vascular clamp 3, which is to restrict the blood flow.

A drawback of related art devices is that the tightening and the loosening of the blood flow into the organs needs to be adjusted manually by the medical operator. Also, operation of the devices to restricting the flow of blood is complicated and consumes time, resulting in increased surgical time that would heighten the risk and burden on the patient.

SUMMARY

Accordingly, there is a need for designing an ischemia control device with an efficient automation function in view of the practical usage, which would substantially obviate one or more of the issues due to limitations and disadvantages of related art ischemia devices. Further, it is preferred that the operation of the ischemia control device would occur automatically without the intervention of a clinician or other medical operators. An object of the present disclosure is to provide an improved ischemia control device having an efficient structure and practical administration of the associated medical procedure. At least one or some of the objectives is achieved by the ischemia device disclosed herein.

Additional features and advantages will be set forth in the description that follows, and in part will be apparent from the description, or may be learned by practice of the invention. The objectives and other advantages of the disclosed ischemia device will be realized and attained by the structure particularly pointed out in the written description and claims thereof, as well as the appended drawings.

In general, the disclosed structures and systems provide for an ischemia control device efficiently suppressing problems such as operation complexity and time management issues associated with manually operated ischemia control devices. The ischemia control device is connected to a control unit that receives inputs from sensors and other surgical devices that senses the state of the organs aimed to achieve ischemia during the medical surgery and other patient conditions. The control unit uses the data inputs, as well as direct inputs from the medical operators, to output opening and closing instructions to the ischemia control device. The actuator on the ischemia control device receives the opening and closing instructions and manipulates the ischemia control device using mechanisms such as motors to open or close the ischemia control device. Therefore, the ischemia control device can be automatically operated using the sensed information to achieve ischemia of the organs or recirculate blood stream to protect the organs from being damaged by the ischemia.

The term "patient," as used herein, comprises any and all organisms and includes the term "subject." A patient can be a human or an animal.

An exemplary embodiment of an ischemia control device comprises a clamp unit that is adjustable between an open state and a closed state to regulate a flow of blood through a blood vessel positioned within the clamp unit, an actuator unit operably connected to the clamp unit to provide a driving force to adjust the clamp unit between the open state and the closed state, and a control unit operably connected to the actuator unit, wherein the control unit receives procedure condition information, generates an opening instruction and a closing instruction, and outputs the opening instruction and the closing instruction.

An exemplary method to restrict a blood flow of an area in a subject comprises attaching a clamp unit to the blood vessel, opening and closing the clamp unit with an actuator unit, outputting opening and closing instructions to the actuator unit through a control unit, and sending procedure condition information to the control unit for constructing the opening and closing instructions.

In some aspects, the opening and closing instructions include instructions to open and close the clamp unit at varying levels, instructions to halt the opening and closing of the clamp unit for a certain period of time, or a combination of such instructions.

In some aspects, procedure condition information includes information from one or more other medical tests or devices, such as image data, video data, ultrasound data, x-ray data, medical device usage information, and direction from an operator, e.g., a clinician performing a procedure.

Other systems, methods, features and advantages will be, or will become, apparent to one with skill in the art upon examination of the following figures and detailed description. It is intended that all such additional systems, methods, features and advantages be included within this description, be within the scope of the present disclosure, and be protected by the following claims. Nothing in this section should be taken as a limitation on those claims. Further aspects and advantages are discussed below in conjunction with the embodiments of the disclosed input device. It is to be understood that both the foregoing general description and the following detailed description of the disclosed input device are examples and explanatory and are intended to provide further explanation of the disclosed ischemia control device as claimed.

BRIEF DESCRIPTION OF THE DRAWING

The following detailed description of preferred embodiments can be read in connection with the accompanying drawings in which like numerals designate like elements and in which.

Figure 1A:
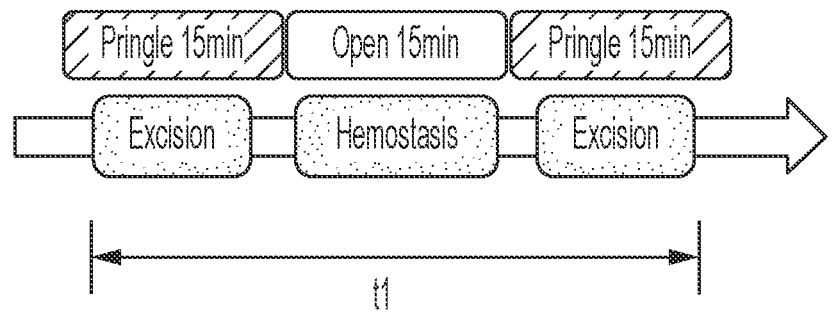
FIG. 1A is a flow chart of a conventional surgery method using manual operation of an ischemia control device.

Throughout all of the drawings, dimensions of respective constituent elements are appropriately adjusted for clarity. For ease of viewing, in some instances only some of the named features in the figures are labeled with reference numerals.

DETAILED DESCRIPTION

FIG. 1A illustrates a flow chart of the conventional surgical procedure using the manual clamping method, wherein the medical operator manually opens and closes (pringles) the clamp unit during the surgery. The clamping of the blood vessels supplying blood stream into the treated organs (e.g. liver) is necessary during the surgical procedure (e.g. excision and coagulation procedures) in order to limit the amount of blood lost during the surgical procedure. The clamp unit is manually operated to first pringle the veins and arteries prior to the surgical procedures being performed. After some time (e.g. 15 minutes), the surgical procedure needs to be halted and clamping of the blood vessels needs to be re-opened in order to lower the risk of necrosis for the treated organs due to the lack of blood flow during the pringle. The medical operators would manually re-open the clamps and perform hemostasis procedures on the treated organs while the treated organs recover using now abundant blood stream. After some time (e.g. 15 minutes), the clamp unit is manually pringled and the surgical procedure is reinstituted. This procedure repeats itself until the surgical procedure is completed. The issue with the above mentioned conventional surgical procedure is that the medical operators need to manually open and close the clamp unit at certain intervals during the surgery, adding workload for the medical operators and adding time to the overall surgery time for the patient.

Figure 2A:
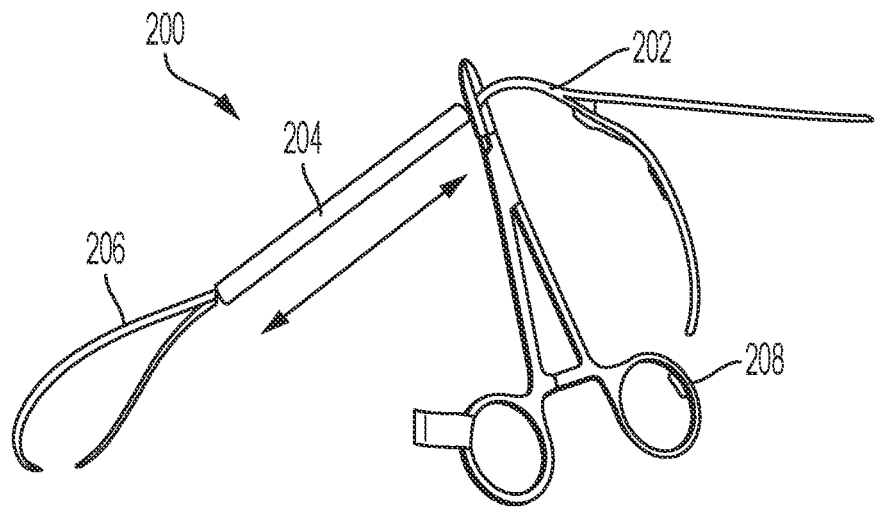
FIGS. 2A to 2C are examples of ischemia control devices used in conventional surgery methods using manual operation of the ischemia control device.
Figure 2B:
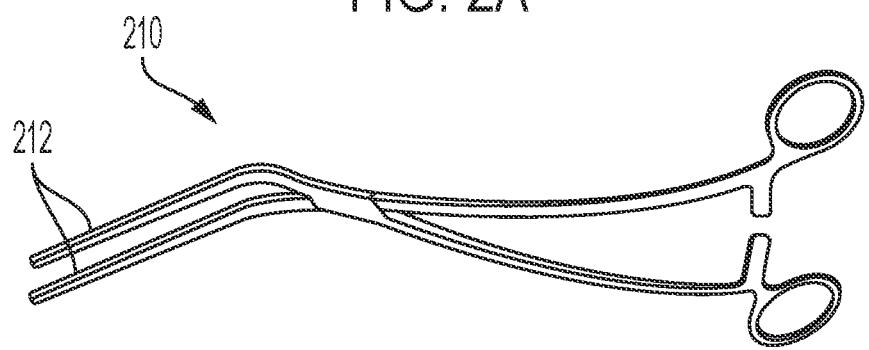
Figure 2C:
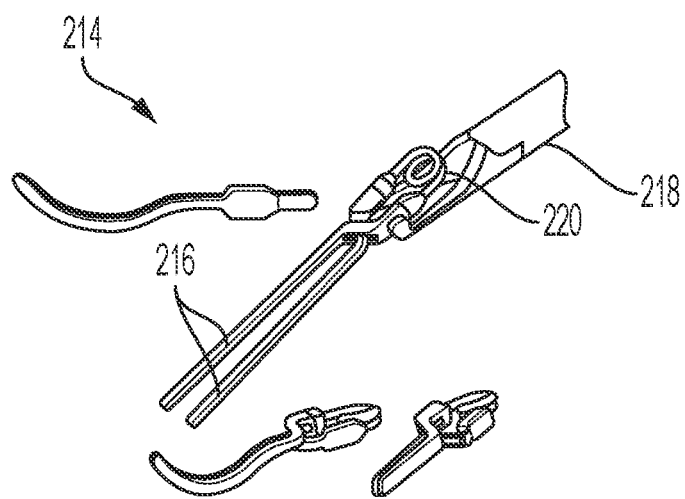

Various manually operated surgical devices and tools can be used to perform the surgical procedures, including the noted Pringle maneuver in hepatoectomy. FIG. 2A illustrates an ischemia control device 200 used for conventional surgical procedure. A tape 202 goes through a shaft 204, forming a loop portion 206 at one end. At the end of the shat 204 opposite from the loop portion 206, forceps 208 is placed for tightening and opening the loop portion 206. In case the loop portion 206 needs to be tightened, the forceps 208 would be used to push the shaft 204 towards loop portion 206 and shortens the amount of tape of the loop portion 206. On the contrary, when the loop portion 206 needs to be loosened, the tweezer 208 would be used to pull back the shaft 204 in the opposite direction of the loop portion 206 and lengthens the amount of tape of the loop portion 206. FIG. 2B illustrates a hemostat forceps 210 used for directly clamping the blood vessels during the conventional surgical procedure. The tips 212 of the hemostat forceps 210 may be directly applied to the veins and arteries of the patient and used to clamp the blood stream going into the treated organs. FIG. 2C illustrates various types of clip devices 214 for directly clamping the blood vessels during the conventional surgical procedure. For example, the clips 216 of the clip device 218 may be directly applied to the veins and arteries of the patient and used to clamp the blood stream going into the treated organs using the clamping mechanism 220.

Figure 1B:
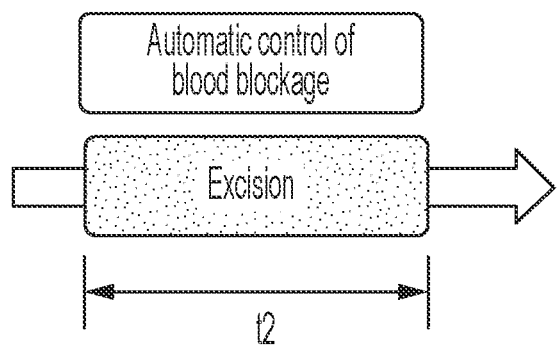
FIG. 1B is a flow chart of a surgery method using automated operation of the ischemia control device as disclosed herein.

FIG. 1B illustrates a flow chart of the surgical procedure using an embodiment of the ischemia control device utilizing the automatic control of blood blockage. Unlike the conventional surgical procedure using manual clamping and as illustrated in FIG. 1A, the opening and closing (pringling) of the clamp unit during the surgery is automated in accordance to the condition of the patient sensed by various devices. The medical operator need not halt the surgical procedure throughout the surgery, since the blood stream going into the treated organs would be automatically controlled. The medical operators need not manually open and close the clamp unit at certain intervals, leading to less workload for the medical operators and shortened surgery time, which would ease risk and burden for the patient. Thus, the time of surgical procedure (t1) in FIG. 1B is less than the time of surgical procedure (t1) in FIG. 1B. Various surgical devices and tools, including those shown in FIGS. 2A-C, can be adapted and configured for automatic operation to automatically control blood flood in accordance to the condition of the patient as sensed by various devices.

Figure 3:
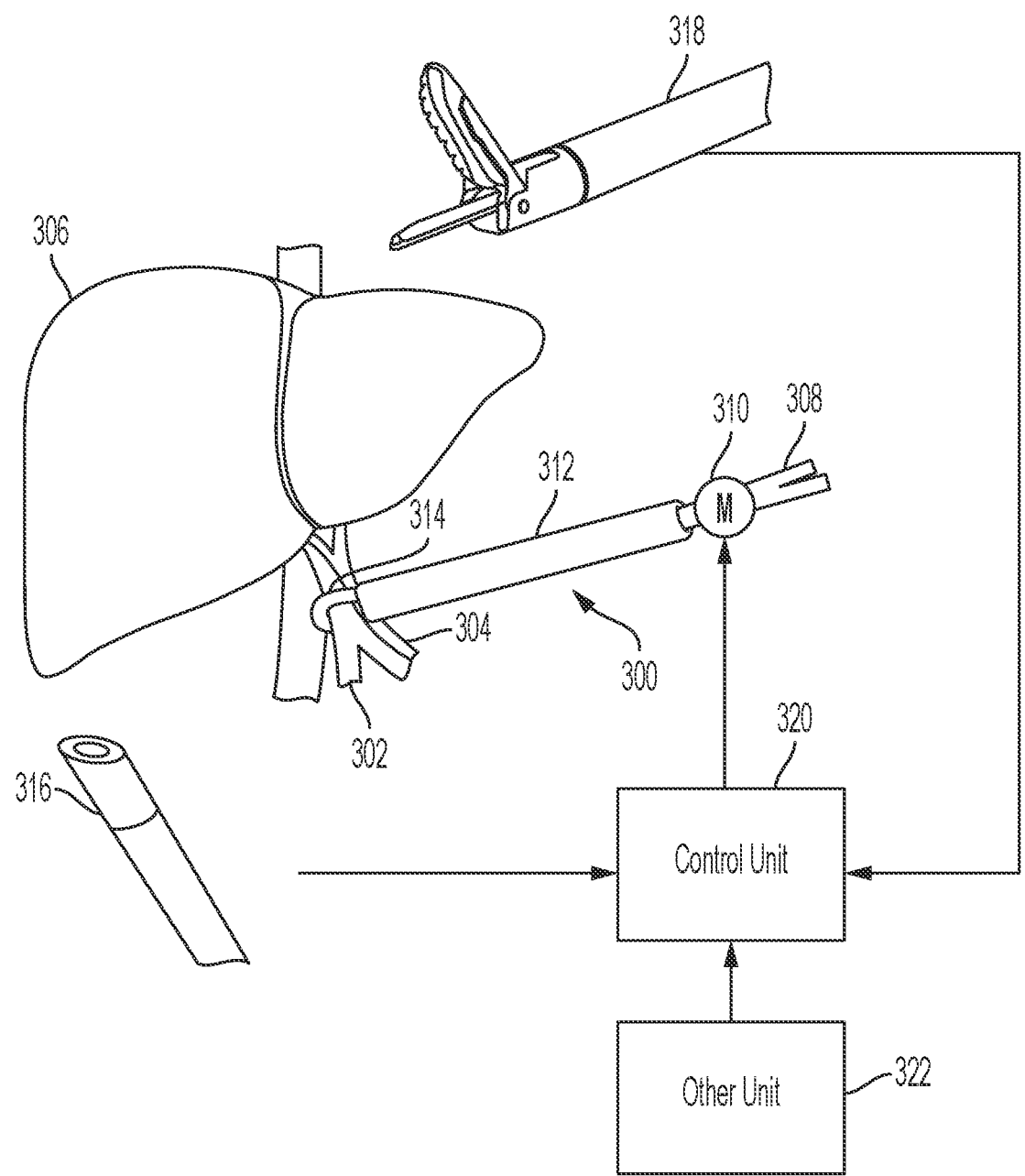
FIG. 3 is an illustration of the embodiment using automated operation of the ischemia control device.

FIG. 3 is an illustration of an ischemia control device 300 attached to the portal vein 302 and hepatic artery 304 of the patient's liver 306. One embodiment of an ischemia control device 300 is comprised of a medical tape 308, an actuator 310, shaft 312, and tape loop 314. The actuator 310 can be, for example, a motor or other device that operates to adjust a relative position of the medical tape 308 and shaft 312, particularly to close and open the tape loop 314. During an endoscopic surgery using an endoscope device 316 and surgical device 318 for the excision and coagulation procedures, the ischemia control device 300 is used to control the blood stream flowing into the liver 306. The tape loop 314 goes around the portal vein 302 and hepatic artery 304 and serves as a clamp unit. Upon actuator 310 receiving an input from the control unit 320 (such as a closing instruction or other input operating signal), the actuator 310 pushes the shaft 312 towards the tape loop 314 using a motor or other device, thereby shortening and tightening the tape loop 314, resulting in ischemia of portal vein 302 and hepatic artery 304. In alternative embodiments, the actuator 310 retracts the tape loop 314 into the shaft 312 using a motor or other device, thereby shortening and tightening the tape loop 314, or the actuator 310 uses a motor or other device to both push the shaft 312 towards the tape loop 314 and to retract the tape loop 314 into the shaft 312, thereby shortening and tightening the tape loop 314.

Upon actuator 310 receiving opening instruction from the control unit 320, the actuator 310 pulls the shaft 312 backwards from the tape loop 314 using the motor, thereby loosening the tape loop 314, resulting in the blood stream to flow back into the portal vein 302 and hepatic artery 304. In alternative embodiments, the actuator 310 extends the tape loop 314 from the shaft 312 using a motor or other device, thereby loosening the tape loop 314, or the actuator 310 uses a motor or other device to both move the shaft 312 away the tape loop 314 and to extend the tape loop 314 from the shaft 312, thereby loosening the tape loop 31.

The control unit 320 may send both opening and closing instructions to the actuator 310. The control unit may send the opening and closing instructions to the actuator intermittently or continuously. Additionally, the actuator can be operated in a control scheme between on (to shorten and tighten or to lengthen and loosen) and off conditions, for example, an on-off control scheme, or can be operated in a control scheme in which the actuator is operated between tightening and loosening conditions, for example, a tightening-loosening control scheme. In optional embodiments, a neutral operating state can be included between tightening and loosening condition, with the actuator stationary and neither tightening nor loosening, for example, a tightening-neutral-loosening control scheme.

The control unit 320 may receive inputs from one or more devices, medical instruments and equipment. In one embodiment, the control unit 320 receives inputs from an endoscope device 316 and uses the input data to determine which instructions should be sent to the actuator 310. The input data received by the control unit from the endoscope device 316 may include procedure condition information such as color of the organs and blood vessels, amount of pressure the organs and blood vessels are under, the amount and speed of blood current, suction volume, and other input data related to the surgery. The control unit 320 may also use inputs from surgery device 318 and other units 322 (e.g. foot switches) for the determination on the instructions to the actuator 310. The input data received by the control unit from the surgery device 318 may include procedure condition information such as duration of the surgery, amount of energy used for the excision or the coagulation procedure, ultrasound data, x-ray data, suction volume, and other data related to the condition of the organs and blood vessels the surgery is performed on. In some embodiments, input data received by the control unit can include both procedure condition information from the endoscope device 316 and surgery device 318.

In another embodiment, the control unit 320 receives inputs from another unit 322, such as image data or video data. Based on that input, and based on that input, procedure condition information is generated. That procedure condition information can, for example, include a closing instruction to allow the actuator unit to close the clamp unit to stop blood flow if a treatment device is seen in the image data or video data, and an opening instruction to allow the actuator unit to open the clamp unit to release the blood flow if no treatment device is seen in the image data or video data.

Controlling the opening and closing of the clamp unit to control a blood flow can occur in conjunction with an operation of an energy device or a suction volume. For example, suction volume may be monitored and, in a state where the suction volume is large (such as where there is a high amount of bleeding), the blood flow may be restricted. In a related way, in a state where the suction volume is low (such as where there is a low amount of bleeding), the blood flow may be released.

Also, monitoring is not limited to looking at the liver or related blood flow, but may be, for example, monitoring for the presence or absence of treatment tools. In this case, the blood flow can be stopped when there is a treatment tool detected in the treatment area and blood flow can be restored when the treatment tool is no longer detected in the treatment area. Also, if the procedure is long and the treatment tool has been detected for a period of time longer than a setpoint time, a warning may be initiated to alert an operator that the procedure should be interrupted and blood flow resumed.

Further, the control unit may be linked with the generator of an energy device. Here, the energy device is operative to provide output when the blood flow is restricted and the output from the energy device is disabled with the blood flow is in the open state. Alternatively, the blood flow may be restricted when the energy device is operating, e.g., is providing an output, and the blood flow may be released when the energy device is not operating, e.g., is not providing an output.

Figure 4:
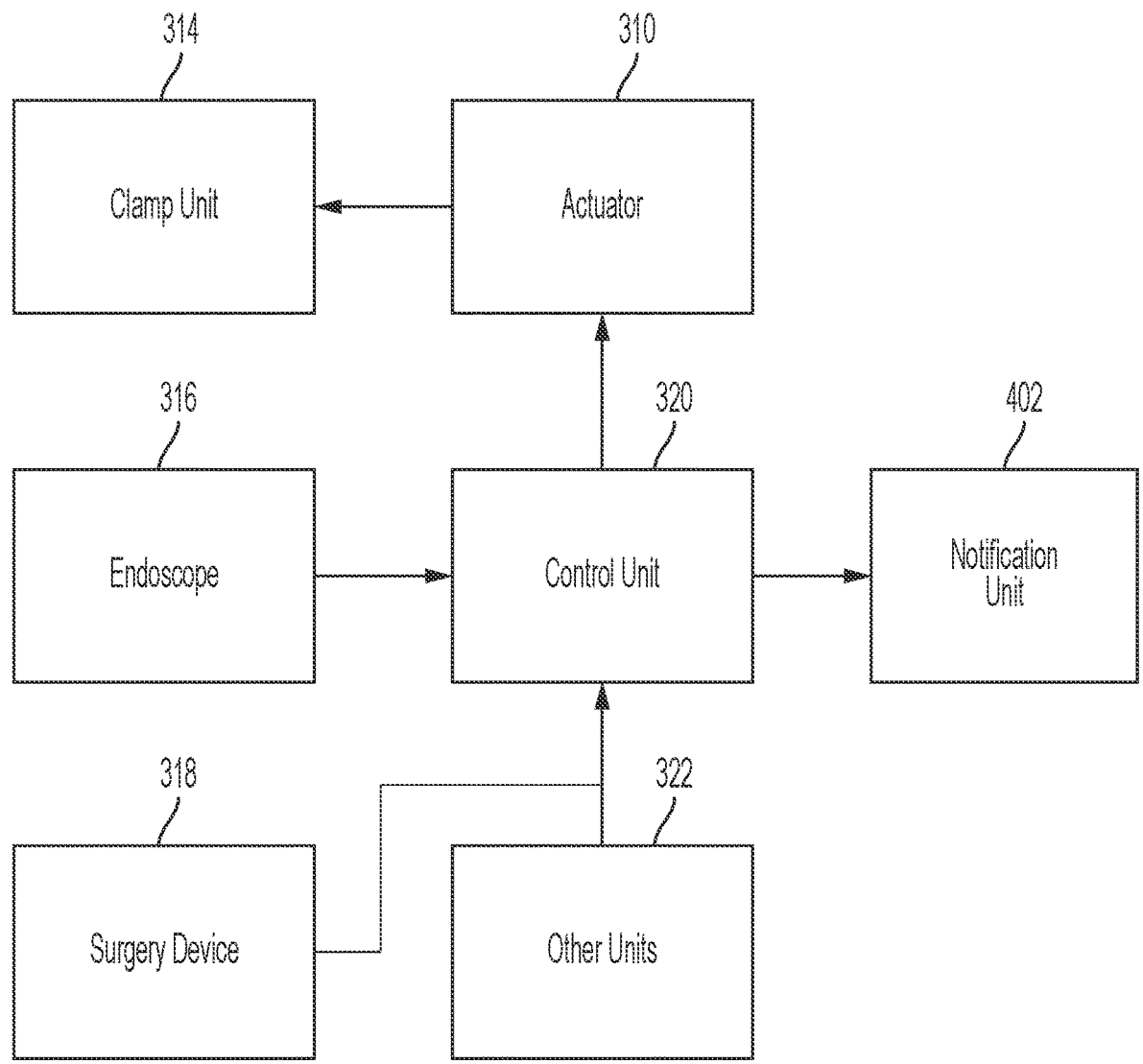
FIG. 4 is a flow chart of the embodiment using automated operation of the ischemia control device.

FIG. 4 is a flow chart of the operation of the ischemia control device 300. The control unit 320 sends opening and closing instructions to the actuator 310 based on the inputs received from the endoscope device 316, surgery device 318, and other units 322. The actuator would actuate the motor to tighten or loosen (or open or close) the clamp unit 314 to achieve ischemia of the blood vessels or allow the blood stream to flow. The control unit may also send instructions to a notification unit 402 alerting the medical operator of the state of the tightening or loosening (or open or close) of the clamp unit 314 through sound, light, or other notification means.

Figure 5A:
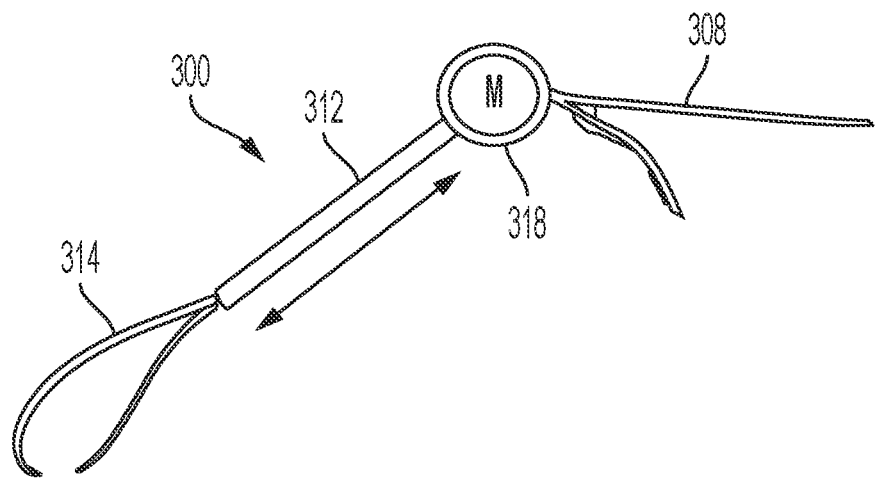
FIGS. 5A and 5B are examples of ischemia control devices used in automated surgery methods.

FIG. 5A illustrates the ischemia control device 300 by itself. The tape loop 314 goes around the blood vessels and serves as a clamp unit by activating the motor in the actuator 310 that pushes the shaft 312 towards the tape loop 314, thereby shortening and tightening the tape loop 314. The tape loop 314 may be loosened by activating the motor in the actuator 310 that pulls the shaft 312 in the opposite direction from the tape loop 314, thereby lengthening and loosening the tape loop 314. The instructions from the control unit 320 may be received by the actuator 318 through wired or through wireless communication.

Figure 5B:
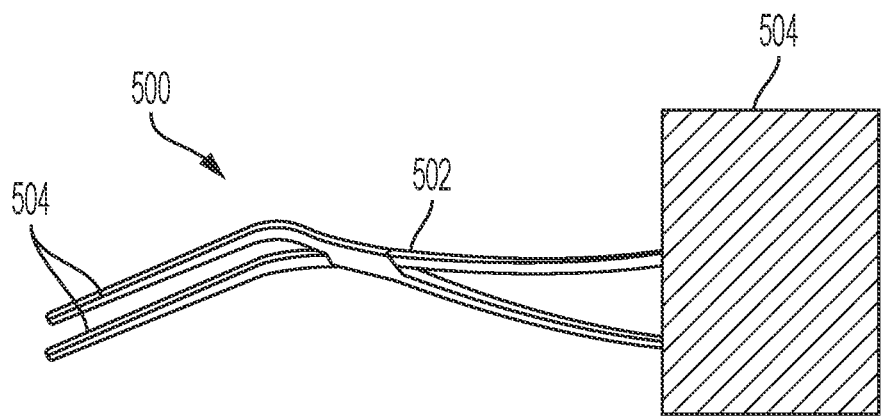

FIG. 5B illustrates another embodiment of an ischemia control device 500. The forceps 502 are connected to an automated open and close device 504 that receives instructions from the control unit 320. Upon receiving a close instruction from the control unit 320, the automated open and close device 504 closes the forceps 502, which results in the tips 504 to close on to the blood vessels aimed at achieving ischemia. Upon receiving an open instruction from the control unit 320, the automated open and close device 504 opens the forceps 502, which results in the tips 504 to open up the blood vessels and blood stream to flow back into the treated organ. The instructions from the control unit 320 may be received by the automated open and close device 504 through wired or through wireless communication.

Figure 6A:
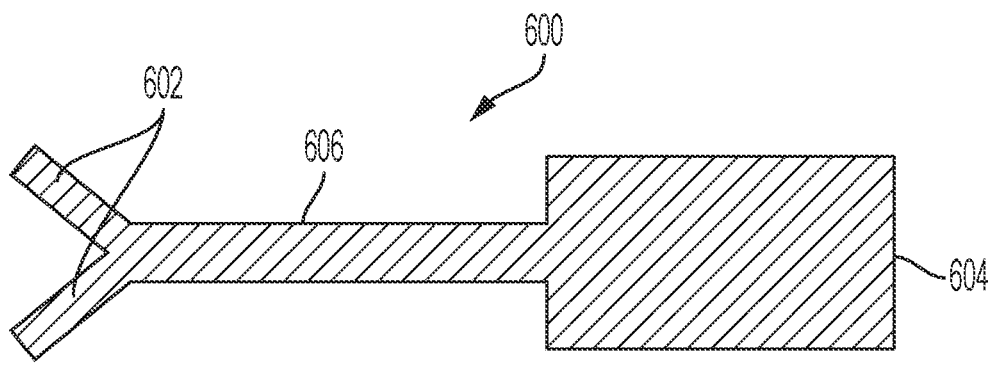
FIGS. 6A and 6B are examples of ischemia control devices used in automated surgery methods.

FIG. 6A illustrates another embodiment of an ischemia control device 600. The clips 602 are connected to an automated open and close device 604 that receives instructions from the control unit 320. Upon receiving a close instruction from the control unit 320, the automated open and close device 604 works on the closing mechanism that goes through shaft 606 that serves to close the clips 602, resulting in the clips 602 to close on to the blood vessels aimed at achieving ischemia. Upon receiving an open instruction from the control unit 320, the automated open and close device 604 opens the clips 602, which results in the tips 504 to open up the blood vessels and blood stream to flow back into the treated organ. The instructions from the control unit 320 may be received by the automated open and close device 604 through wires or through wireless communication.

Figure 6B:
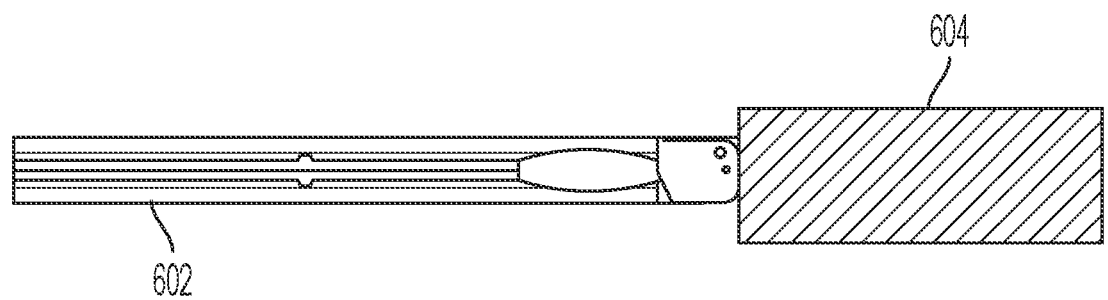
Figure 7:
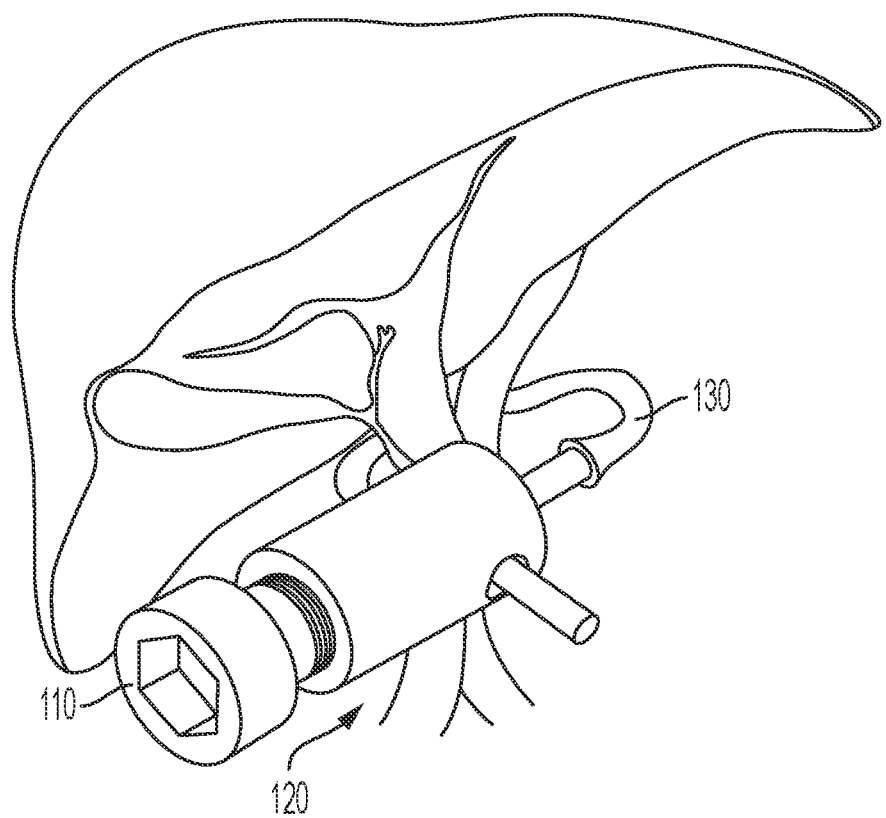
FIGS. 7 and 8 are illustrations of related art ischemia devices.
Figure 8:
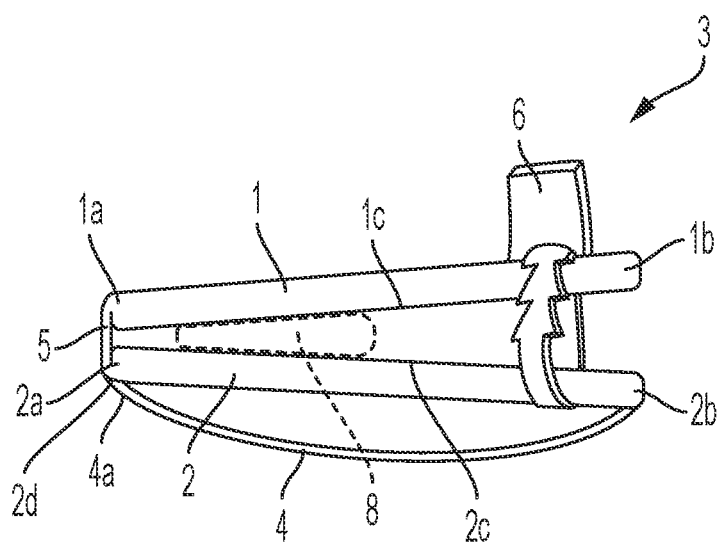

FIG. 6B illustrates another embodiment of the ischemia control device 600. The clips 602 are connected to an automated open and close device 604 that receives instructions from the control unit 320. Upon receiving a close instruction from the control unit 320, the automated open and close device 604 works on the closing mechanism that goes through shaft 606 that serves to close the clips 602, resulting in the clips 602 to close on to the blood vessels aimed at achieving ischemia. Upon receiving an open instruction from the control unit 320, the automated open and close device 604 opens the clips 602, which results in the tips 504 to open up the blood vessels and blood stream to flow back into the treated organ. The instructions from the control unit 320 may be received by the automated open and close device 604 through wires or through wireless communication.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:
1. An ischemia control device, comprising:
a control unit,
wherein the control unit is configured to:
receive information that includes a monitored suction volume for suctioning bleeding,
based on the received information, generate one of a clamp opening instruction and a clamp closing instruction, and
output to a clamp unit one of the clamp opening instruction and the clamp closing instruction to regulate a flow of blood through a blood vessel clamped by the clamp unit.

2. The ischemia control device according to claim 1, further comprising the clamp unit is adjustable between an open state and a closed state based on the outputted clamp opening instruction and outputted clamp closing instruction, and
wherein the clamp unit includes one or more of a tape, a tube, a forceps, and a clip.

3. The ischemia control device according to claim 1, further comprising the clamp unit is adjustable between an open state and a closed state based on the outputted clamp opening instruction and outputted clamp closing instruction,
wherein the clamp closing instruction causes the clamp unit to clamp the blood vessel, and
wherein the blood vessel is a portal vein or a hepatic artery.

4. The ischemia control device according to claim 1, wherein the control unit is further configured to:
generate a clamp intermediate instruction, and
output to the clamp unit the generated clamp intermediate instruction to regulate the flow of blood through the blood vessel clamped by the clamp unit.

5. The ischemia control device according to claim 4, further comprising the clamp unit is adjustable between an open state and a closed state based on the outputted clamp opening instruction and outputted clamp closing instruction, and
wherein the clamp intermediate instruction places the clamp unit in an intermediate state that is between the open state and the closed state.

6. The ischemia control device according to claim 5, wherein the control unit is further configured to stop at least one of the open state, the closed state, and the inter mediate state.

7. The ischemia control device according to claim 2, wherein the control unit is further configured to:
generate a notifying instruction to notify an operator of a status of the clamp unit as in the open state or in the closed state.

8. The ischemia control device according to claim 1, wherein the information includes one or more of usage information of a surgery energy device and direction from an operator.

9. The ischemia control device according to claim 1, wherein the control unit is further configured to periodically output one of the generated clamp opening instruction and the generated clamp closing instruction.

10. The ischemia control device according to claim 1, further comprising an actuator unit operably connected to the clamp unit to provide a driving force to adjust the clamp unit between an open state and a closed state.

11. The ischemia control device according to claim 1, wherein the information further includes at least one of (i) a color of an organ or the blood vessel, (ii) an amount of pressure in the blood vessel, (iii) an amount of pressure in the blood vessel of the organ, (iv) an a mount of the flow of blood through the blood vessel, and (v) a speed of the flow of blood through the blood vessel.

12. The ischemia control device according to claim 1, wherein the information further includes one or more of image data or video data, and wherein the control unit is further configured to:
   determine if a treatment device is detected in one or more of the image data or the video data; and
   in response to determining that the treatment device is detected in one of the image data and the video image, generating the clamp closing instruction to be outputted to the to the clamp unit to regulate the flow of blood through the blood vessel clamped by the clamp unit.

13. The ischemia control device according to claim 12, wherein the control unit is further configured to:
   in response to determining that the treatment device is not detected in one of the image data and the video image, generating the clamp opening instruction to be outputted to the clamp unit to regulate the flow of blood through the blood vessel clamped by the clamp unit.

14. The ischemia control device according to claim 1, wherein the information includes a first operational information corresponding to a surgery energy device operating, and a second operational information corresponding to the surgery energy device not operating,
   wherein the control unit is further configured to:
      determine if the received information is one of the first operational information or the second operational information,
      in response to determining that the received information is the first operational information, generating the clamp closing instruction, and
      in response to determining that the received information is the second operational information, generating the clamp opening instruction.

15. The ischemia control device according to claim 14, wherein the first operational information corresponds to the surgery energy device providing an output for an excision or coagulation procedure, and the second operational information corresponds to the surgery energy device not providing the output.

16. The ischemia control device according to claim 1, wherein the control unit is further configured to:
   determine if the monitored suction volume is larger or smaller than a predetermined volume,
   generate the clamp closing instruction in response to determining that the monitored suction volume is larger than the predetermined volume, and
   generate the clamp opening instruction in response to determining that the monitored suction volume is smaller than the predetermined volume.

17. An ischemia control device, comprising:
   a control unit configured to:
      receive information including a monitored suction volume for suctioning bleeding and one or more of image data or video data,
      determine if a treatment device is detected in one or more of the received image data or the received video data,
      in response to determining that the treatment device is detected, generate a clamp closing instruction, and
      output to a clamp unit the generated clamp closing instruction to regulate a flow of blood through a blood vessel clamped by the clamp unit,
   wherein the treatment device is different from the clamp unit.

18. The ischemia control device according to claim 17, wherein the control unit is further configured to:
   in response to determining that the treatment device is not detected, generate a cla mp opening instruction; and
   output the generated clamp opening instruction to the clamp unit.

19. An ischemia control device, comprising:
   a control unit configured to:
      receive information from a surgery energy device,
      based on the received information, generate one of a clamp opening instruction and a clamp closing instruction, and
      output to a clamp unit one of the generated clamp opening instruction and the generated clamp closing instruction to regulate a flow of blood through a blood vessel clamped by the clamp unit,
   wherein the surgery energy device is different from the clamp unit, and
   wherein the information includes a monitored suction volume for suctioning bleeding.

20. The ischemia control device according to claim 19, wherein the control unit is further configured to:
   determine if the monitored suction volume is larger or smaller than a predetermined volume,
   in response to determining that the monitored suction volume is smaller than the predetermined volume, generate the clamp opening instruction, and
   in response to determining that the monitored suction volume is larger than the predetermined volume, generate the clamp closing instruction.

* * * * *